(12) United States Patent
Lange et al.

(10) Patent No.: US 6,778,279 B2
(45) Date of Patent: Aug. 17, 2004

(54) INLINE SAGNAC FIBER OPTIC SENSOR WITH MODULATION ADJUSTMENT

(75) Inventors: Charles Lange, Glendale, AZ (US); Steve Sanders, Scottsdale, AZ (US); Dick Ang, Glendale, AZ (US); Lee K. Strandjord, Tonka Bay, MN (US)

(73) Assignee: Honeywell International, Inc., Morristown, NJ (US)

( * ) Notice: Subject to any disclaimer, the term of this patent is extended or adjusted under 35 U.S.C. 154(b) by 85 days.

(21) Appl. No.: 10/078,741

(22) Filed: Feb. 19, 2002

(65) Prior Publication Data

US 2003/0169956 A1 Sep. 11, 2003

(51) Int. Cl.[7] .............................................. G01B 9/02
(52) U.S. Cl. ...................................................... 356/483
(58) Field of Search ................................. 356/477, 482, 356/485, 35.5, 483; 250/227.19, 227.27

(56) References Cited

U.S. PATENT DOCUMENTS

| | | | |
|---|---|---|---|
| 4,572,949 A | * 2/1986 | Bowers et al. | 356/482 |
| 4,787,741 A | * 11/1988 | Udd et al. | 356/483 |
| 4,957,362 A | * 9/1990 | Peterson | |
| 5,734,469 A | 3/1998 | Strandjord | |
| 5,894,531 A | * 4/1999 | Alcoz | 356/477 |
| 6,175,410 B1 | 1/2001 | Szafraniec et al. | |
| 6,211,963 B1 | 4/2001 | Kaliszek et al. | |
| 6,459,486 B1 | * 10/2002 | Udd et al. | 356/483 |

FOREIGN PATENT DOCUMENTS

GB 2 183 417 A * 6/1987

OTHER PUBLICATIONS

Karolous, "Die physikalischen Grundlagen der elektro–optischen Entfernungsmessung", Verlag Der Bayerischen Akademie Der Wissenschaften, Germany 1958, 5 pgs. and English translation of specified portions.*

Collins et al., "A simple laser diode ranging scheme using an intensity modulated FMCW approach", Measurement Science & Technology, Dec. 1993, vol. 4, No. 12, pp. 1437–1439.*

* cited by examiner

Primary Examiner—Samuel A. Turner
(74) Attorney, Agent, or Firm—Schiff Hardin LLP (57) ABSTRACT

A method is provided for sensing an environmental effect upon a sensing element and includes exposing the sensing element into the environmental effect, producing a light signal in the sensing element, modulating the light signal with a modulation signal, and determining a path length of the light signal as a function of the modulation signal. A fiber optic sensor is provided that includes a light source producing a light, a sensing element optically coupled to the light source such that the light propagates through the sensing element, a detector optically coupled to the sensing element. The detector detects light intensity propagating in the sensing element. An electronics processor receives the detector output and produces a modulation signal for the light. The processor further produces an output signal indicative of the environmental effect as a function of the modulation signal.

23 Claims, 10 Drawing Sheets

INLINE SAGNAC FIBER OPTIC SENSOR WITH MODULATION ADJUSTMENT

BACKGROUND OF THE INVENTION

1. Technical Field

The invention relates generally to optical sensors, and particularly to interferometric sensors for determining environmental effects.

2. Description of the Related Art

As fiber optics become more prevalent, various types of optical sensors have become increasingly common. Indeed, various types of sensors detect fiber lengths, locations of breaks/cracks/inconsistencies in optical fibers, temperature, pressure, fiber expansion, attributes of chemical species, and the like.

Optical fibers may be subjected to various external effects that produce geometric (e.g., size, shape) and/or optic (e.g., refractive index, mode conversion) changes to the fiber depending upon the nature and the magnitude of the perturbation. While these effects are often considered to be parasitic (i.e., noise-causing) in communications applications, the fibers response to external influence may be increased in sensing applications so that the resulting change in optical characteristics can be used as a measure of the external effect.

Optical fibers may therefore act as transducers that convert effects such as temperature, stress, strain, rotation or electric and magnetic currents into corresponding changes in optical effects. Since amplitude (intensity), phase, frequency and polarization typically characterize light, any one or more of these parameters may undergo a change due to external effects. The usefulness of the fiber optic sensor therefore depends upon the magnitude of this change and upon the ability to measure and quantify the change reliably and accurately.

Many different types of sensors based upon fiber optic technologies are well known. Among the sensor techniques that have been known for some time are interferometers, which typically detect various phenomena by sensing phase changes or interference patterns between multiple optical signals passing through the sensor. Interferometers have been widely used in the past to determine distance, slope, rotation, and the like. Since about 1980, interferometric fiber optic gyroscopes (IFOGs) have been widely used to detect rotation. Such sensors have proven to be particularly useful for generating inertial navigation data that can be used to guide aircraft, automobiles, other vehicles, downhole drilling apparatus, robots and the like. Various embodiments of IFOGs are described in many patents, including U.S. Pat. Nos. 6,211,963 and 6,175,410, which are incorporated herein by reference.

Fiber optic strain sensors based upon fiber Bragg gratings have similarly been used for several years. Such sensors typically immerse a Bragg grating coupled to an optical sensor into an environment to be sensed. As the environment changes the optical properties of the Bragg grating, the wavelength of light reflected off the grating changes. Hence, an output based upon the wavelength of reflected light may be indicative of some property of the environment sensed. Such sensors have exhibited a number of marked disadvantages, however, in that they are typically expensive, difficult to manufacture, and require measurements of light wavelength, which is difficult to measure accurately in practice. Accordingly, sensors based upon Bragg gratings have typically not been suitable for most low-cost applications. A relatively simple and low-cost interferometric sensor that is accurate and that has a high resolution is therefore desired for a variety of applications.

BRIEF SUMMARY OF EXEMPLARY EMBODIMENTS

According to various exemplary embodiments, a technique for sensing an environmental effect upon a sensing element suitably includes exposing the sensing element into the environmental effect, producing a light signal in the sensing element, modulating the light signal with a modulation "drive" signal, and determining a path length of the light signal from the resulting modulated signal on a sensing optical detector, as a function of the modulation drive signal. According to further exemplary embodiments, a fiber optic sensor suitably includes a light source producing a light, a sensing element optically coupled to the light source such that the light propagates through the sensing element, a detector optically coupled to the sensing element. The detector is configured to detect the intensity of the light propagating in the sensing element and to produce a detector output indicative of the intensity; and the electronics receive the detector output and produce a modulation signal for the light based on it, and the electronics further produce an output signal indicative of the environmental effect as a function of the modulation signal.

BRIEF DESCRIPTION OF THE DRAWING FIGURES

The various features and advantages are described below in the following detailed description of illustrative embodiments to be read in conjunction with the accompanying drawing figures, in which like reference numerals are used to identify the same or similar parts in the similar views.

DETAILED DESCRIPTION OF EXEMPLARY EMBODIMENTS

The present invention may be described in terms of functional block components and various processing steps. Such functional blocks may be realized by any number of hardware and/or software components configured to perform the specified functions. For example, the present invention may employ various integrated circuit or optical components, e.g., memory elements, processing elements, logic elements, look-up tables, and the like, which may carry out a variety of functions under the control of one or more microprocessors or other control devices. Similarly, the software elements of the present invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, optical configuration, signal processing, data processing and the like.

The particular implementations shown and described in this specification are examples of the invention and are not intended to otherwise limit the scope of the present invention in any way. For the sake of brevity, conventional electronics, optics, software development and other functional aspects of the systems (and components of the individual operating components of the systems) may not be described in detail. Furthermore, the connecting lines shown in the various figures provided are intended to represent exemplary functional relationships and/or physical or logical couplings between the various elements. Many alternative or additional functional relationships, physical connections or logical connections may be present in a practical sensor device. Moreover, no item or component is essential to the practice of the invention unless the element is specifically described as "essential" or "critical".

According to various exemplary embodiments of the invention, a fiber optic sensor (and an associated method of operation) is produced that provides a highly reciprocal light path for two or more light beams in an interferometer. The paths taken by the various beams propagating through the optical portion of the sensor may be identical except for a portion of the optical circuit that induces a modulation between the beams. In various embodiments, a modulation technique that is based upon the "proper" frequency may be sensitive to minute changes in the length of the optical path taken by the light in the interferometer. Such a sensor may be useful in a variety of applications including, without limitations, in a fiber break tester, LIDAR (Light Detection and Ranging, a remote sensing technique that uses laser light in much the same way that sonar uses sound, or radar uses radio waves), optical transducer circuit, or in any number of pressure, temperature or chemical sensing applications. Any of the various conventional techniques (such as manufacturing techniques, modulation techniques and signal processing techniques) that have been used in conjunction with interferometric sensors (such as IFOGs) may be used in conjunction with the present invention. Moreover, bulk optics components (couplers and the like) may be substituted for any of the components described in various alternate embodiments.

Figure 1:
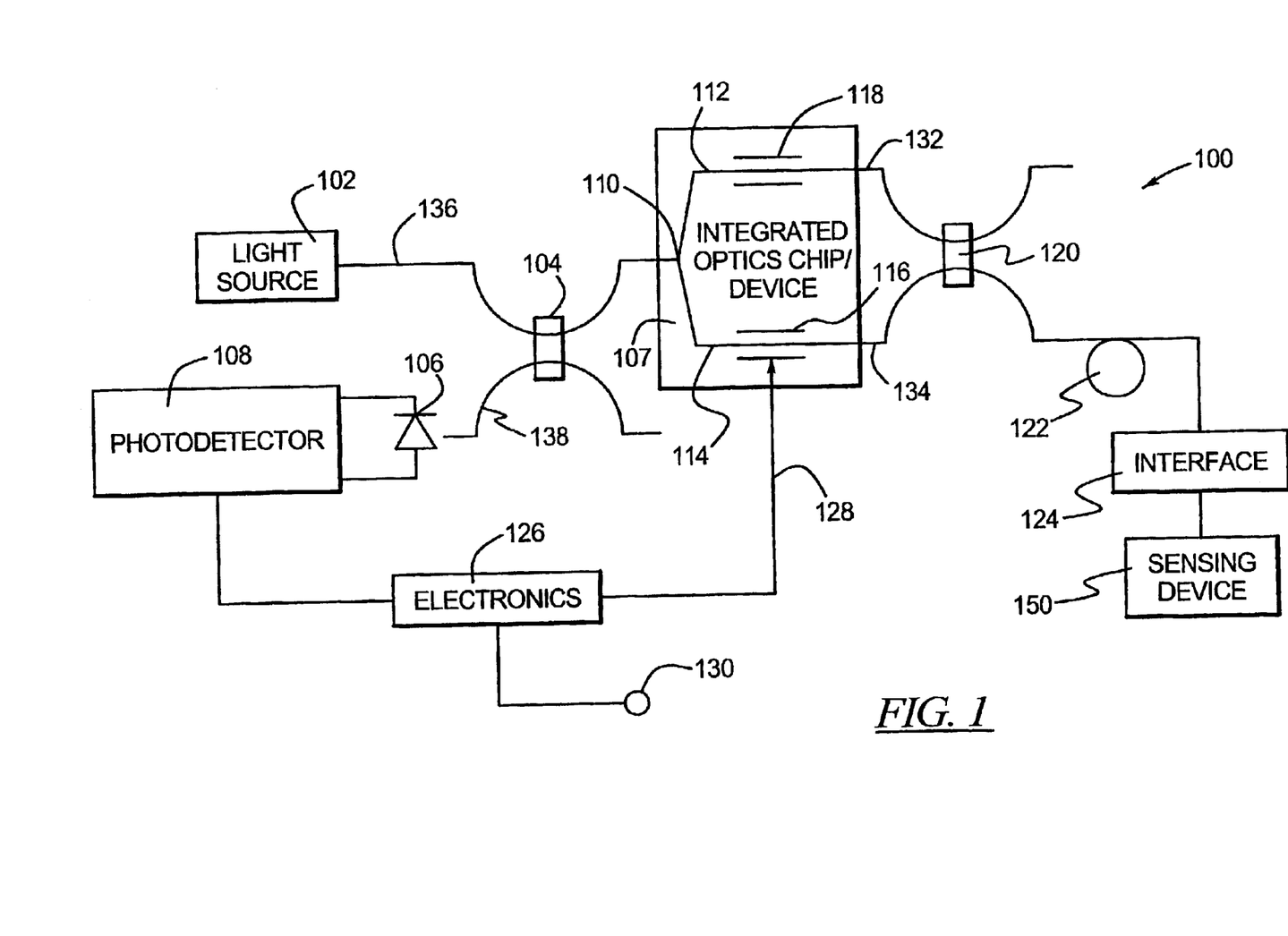
FIG. 1 is a block diagram of an exemplary sensor.

FIG. 1 is a schematic of a first exemplary embodiment of an interferometric sensor. With reference to FIG. 1, an exemplary sensor 100 suitably includes a light source 102, a first optical coupler 104, a photodetector circuit 108 that may be coupled to a photodiode 106, an integrated optics chip/device 107, a second coupler 120, an optional delay loop 122, an interface 124 and a suitable electronics processor 126 providing a sensor output 130. Light generated by light source 102 suitably passes through sensor 100 to a device 150 (such as an optical fiber, lens, other sensing element, or the like) that may be coupled to interface 124. Integrated optics chip 107 may include a "Y" junction 110 and one or more phase modulators (e.g., a first phase modulator 118 and second phase modulator 116), as shown in FIG. 1. In such embodiments, Y-junction 110 separates light into two components (traveling on a first light path 112 and second light path 114, respectively) that may be individually modulated to induce phase differences between the two beams. The separated beams may be re-combined at the second optical coupler 120 so that the only non-reciprocal portion of sensor 100 is that portion between Y-junction 110 and coupler 120.

After light is provided to the sensing device 150 coupled to interface 124, reflected light from the device 150 may be returned through the optical portion of sensor 100 to detector 106, which produces a signal indicative of the phase difference between the separate beams as appropriate. This phase difference may be observed and processed by electronics processor 126 to determine the total path length of the light traveling through the device 150. This phase difference may also be used to compute a modulation signal 128, as described more fully below.

Light source 102 may be any device capable of producing light in sensor 100 such as a laser diode (LD), a light emitting diode (LED), a super-luminescent diode (SLD) or the like. Although coherent light or light having any coherence length could be used, various embodiments of light source 102 produce white light with a relatively low coherence length (typically on the order of several hundred microns or less) to create desired interference patterns at detector 106, as described more fully below. Light generated by light source 102 is split into at least four components in sensor 100 corresponding to: (1) first light path 112 out, first light path 112 returning; (2) first light path 112 out, second light path 114 returning; (3) second light path 114 out, first light path 112 returning; and (4) second light path 114 out, second light path 114 returning. If the coherence of light source 102 is properly selected such that the coherence length of light source 102 is significantly shorter than the differential path length between light paths 112 and 114, then only the interference of paths (2) and (3) above will produce a desired signal at photodetector 108. The specific bandwidth of light source 102 is relative to the particular application, but in various exemplary embodiments light source 102 is a fiber light source, laser diode (LD), or super-luminescent diode (SLD). Light source 102 is coupled to optical fiber 136 through any conventional technique.

Optical fibers (such as fibers 132, 134, 136 and 138) interconnecting the various components in sensor 100 may be any sort of optical fiber capable of directing light between the components. In various embodiments, the optical fibers are single mode fibers capable of directing a single optical mode such that various filters are not required in sensor 100 to isolate desired modes for signal processing. Optical fibers may also be polarization maintaining fibers or polarizing fibers, particularly in embodiments that do not include a polarizer in the optical circuit (such as the embodiment shown in FIG. 1). If polarization maintaining optical fiber is not used, various alternate embodiments might include an optical polarizer anywhere in the optical circuit such as in integrated optics chip 107 or between the first optical coupler 104 and optics chip 108.

Couplers 104 and 120 may be any coupling devices capable of joining optical signals propagating on separate fibers. Exemplary couplers include conventional 2×2 couplers available from the Sifam corporation, JDS Uniphase, Gould, etc. Alternatively, fibers 136/138 and 132/134 may be joined to form a coupler by stripping the cladding off of each fiber in the relevant position for the coupler, placing the two fiber cores together, and melting the cores together with the application of heat and optional tensile pressure. Light entering couplers 104/120 from either port in a first direction is suitably divided into two portions, with each portion exciting the coupler on a port on the opposite side of the coupler. In various embodiments, the light is split approximately equally between the two opposing ports. In other embodiments, one of the ports receives more or even all of the light passing through the coupler.

Integrated optics chip (IOC) 107 suitably includes a y-junction and at least one modulator 116/118. In various embodiments, IOC 107 is formed from lithium niobate (LiNO3) or another material that affects the speed of light in response to an applied electric potential. Alternatively, IOC 107 may be any conventional optical splitter/modulator combination such as a model #SG-150-1-1=k IOC available from the JDS Uniphase corporation of San Jose, Calif. IOC 107 suitably includes a waveguide (shown as a solid line in FIG. 1) for guiding light from source 102 through the chip. The path may include a y-junction 110 that splits light from coupler 104 into two paths 112 and 114. Y-junction 110 may also re-combine light received upon paths 112 and 114, as appropriate. One or more optical phase modulators 116/118 (which may be implemented as electrodes in IOC 107 near paths 114/112) may also be provided to produce phase shifts in light passing through paths 114/112, respectively, in response to modulation signals produced by electronics processor 130. In various alternate embodiments and as described more fully below, IOC 107 may be replaced with different but equivalent components such as couplers, splitters, modulators (such as piezoelectric modulators), polarizers, and the like.

Optional delay loop 122 may be included in various embodiments, and is discussed more fully below, particularly in conjunction with FIG. 9. Delay loop 122 may be a physical loop or coil of optical fiber that adds to the optical path length traveled by light in sensor 100.

Interface 124 is any interface to a device 150 that is being sensed. For example, interface 124 could be an interface to a lens arrangement to produce a lidar, or 124 could be an interface to an external optical fiber that can be used to detect breaks in the optical fiber. It will be appreciated that interface 124 may be a mere fiber splice in various embodiments, or 124 may be omitted in embodiments where sensor 100 is formed as an integral part of an optical fiber or the like.

Photodetector 108 is any circuit capable of detecting the intensity (i.e., amplitude) of light emanating from fiber 138. In various embodiments, photodetector circuit 108 suitably includes a photodiode or avalanche photodiode 106 that conducts an electric current in response to the intensity of incident light. Photodetector circuit 108 may also include circuitry or other components to generate a digital or analog signal that is provided to electronics 130, as appropriate. Numerous conventional photodetector circuits 108 have been developed for use with fiber optic gyroscopes or other sensors that may be applicable to sensor 100. In various embodiments, photodetector 108 is a model PN 03000040-999 photodiode available from the Epitaxx corporation of West Nepian, Ontario, Canada. Photodetector 108 response may be dependent upon the wavelength of incident light, so photodetector 108 may be selected to correspond to the wavelength of light propagating through sensor 100.

Electronics processor 126 suitably includes any processing circuitry suitable for calculating sensor output 130 and feedback signal 128 such as a microprocessor, a microcontroller, a digital signal processor, a programmed array logic (PAL), an application specific integrated circuit (ASIC), a programmable gate array (PGA) or any other device. In an exemplary embodiment, electronics processor 126 suitably includes a microprocessor or digital signal processor, which will typically be provided in conjunction with an associated memory and circuitry for addressing, input/output, and the like. Various embodiments of electronics 126 have been disclosed in conjunction with various fiber optic gyroscope devices, and any fiber optic gyroscope electronics scheme could be readily adapted for use in sensor 100. In various embodiments, electronics 126 suitably integrate, filter and process the output of photodetector 108 to produce output signal 130. Even though FIG. 1 shows sensor 100 operating as a feedback driven or "closed loop" sensor, alternate embodiments will use an "open loop" (i.e., no feedback) configuration that generates modulation (feedback) signal 128 without regard to the output of photodetector 108. While closed loop operation may add to the stability and resolution of sensor 100, closed loop operation may be more complex than open loop operation in many embodiments, however.

With continued reference to FIG. 1, sensor 100 suitably functions by passing light generated from light source 102 through coupler 104 to IOC 107. Light is suitably split by Y-junction 110 into a beam passing through waveguide (first light path) 112 and a beam passing through waveguide (second light path) 114. At least one of the beams is modulated by phase modulator 116 in response to modulation signal 128, as described more fully below, to create a shift in the phase of the light beam. The two beams are re-combined at coupler 120, where light is passed through optional delay loop 122 to interface 124 and onto the sensed device 150. Light reflected from the sensed device re-enters sensor 100 at interface 124, where the light passes through optional delay loop 122 before being split at coupler 120. The reflected light is split into a component passing on fiber 132 and waveguide 112, and a component passing on fiber 134 and waveguide 114, where a modulation may be applied by modulator 116. The two components are suitably re-joined at Y-junction 110 and passed through coupler 104 to detector 108.

As noted above, light generated by light source 102 is split into at least four components corresponding to: (1) first light path 112 out, first light path 112 returning; (2) first light path 112 out, second light path 114 returning; (3) second light path 114 out, first light path 112 returning; and (4) second light path 114 out, second light path 114 returning. The two components of light passing through path (2) and light passing through path (3) will traverse identical distances. Moreover, light passing on these paths will receive identical drive modulations from modulator 116, with the exception that the modulation will be shifted in time by an amount that is related to the time delay for the beam to pass through the sensed device. Hence, the difference in modulations applied to the two beams is due to this time delay, which is related to the length of the sensed device. This modulation difference manifests itself as a time-varying waveform on the photodetector 108. By suitable processing of the time varying waveform on the photodetector 108, the length of the path traversed by the beams can be calculated. Processing of the time varying waveform on the photodetector 108 may include use of a feedback mechanism to adjust the drive modulation applied to account for this delay, The path length so measured can be used to determine the length of an optical fiber or the location of a break in an optical fiber. Alternatively, the path length can be used in any other type of sensor such as a LIDAR, transducer sensor, or the like.

Figure 2A:
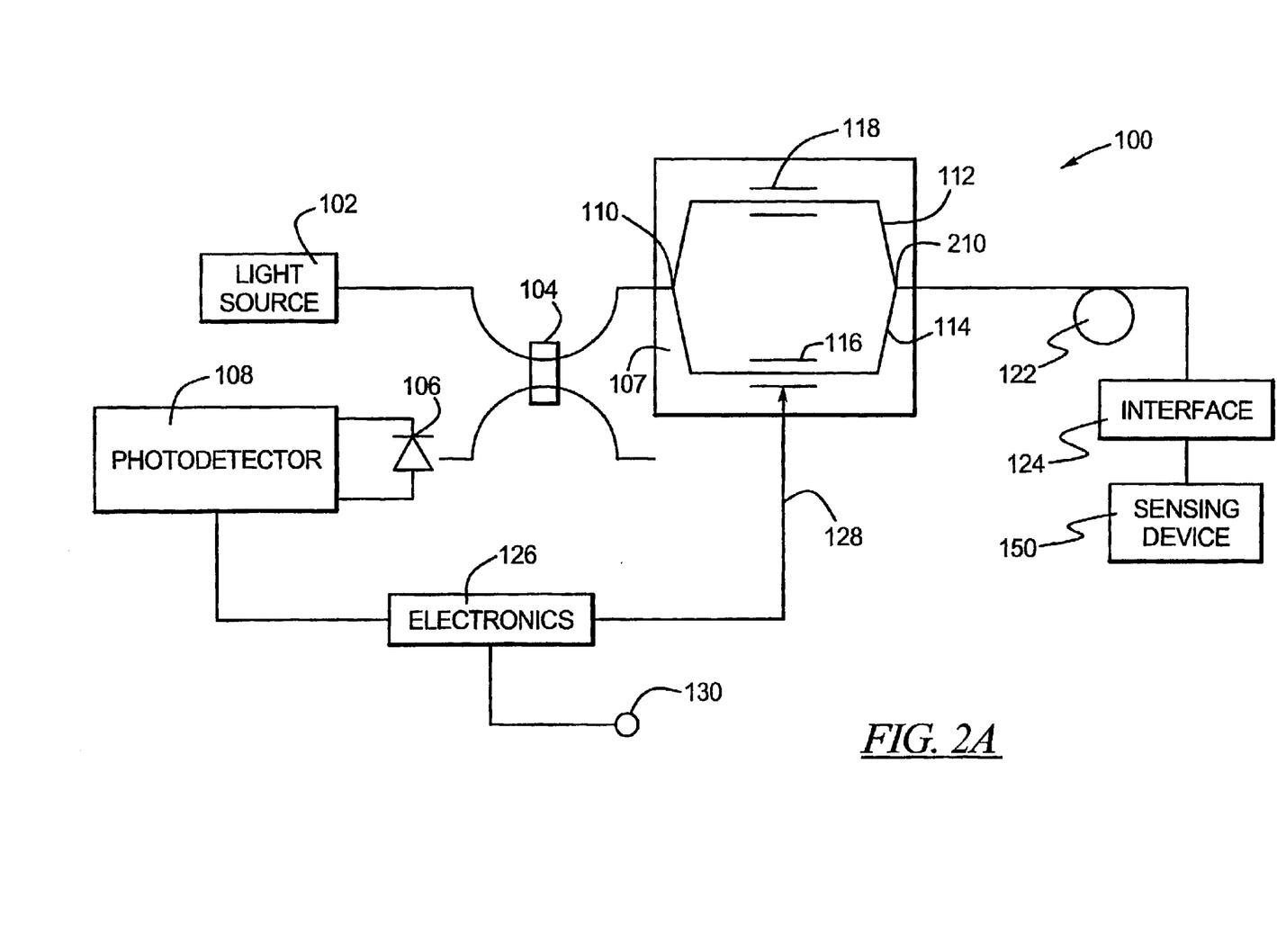
FIG. 2A is a block diagram of a second exemplary embodiment of a sensor.
Figure 2B:
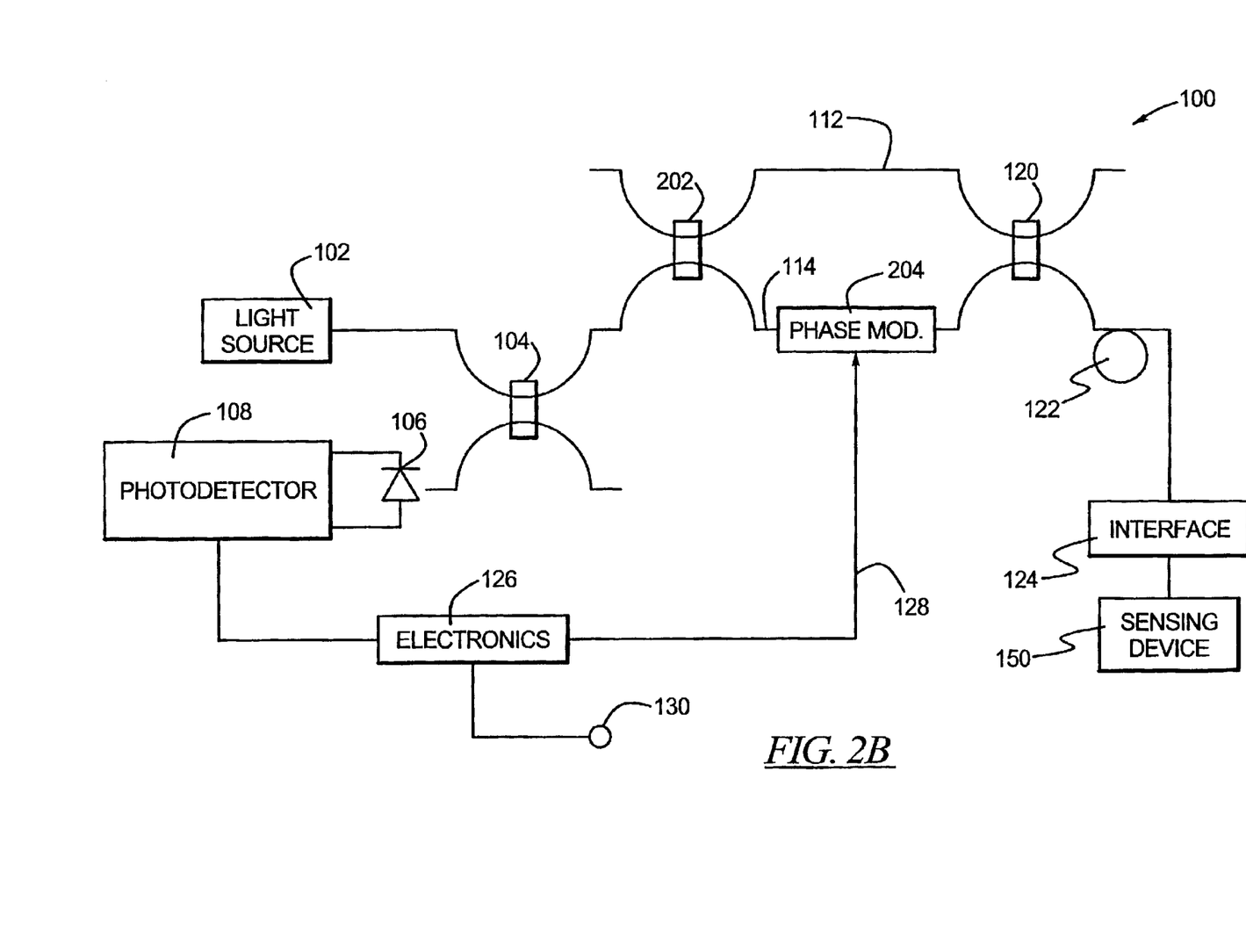
FIG. 2B is a block diagram of a third exemplary embodiment of a sensor.
Figure 2C:
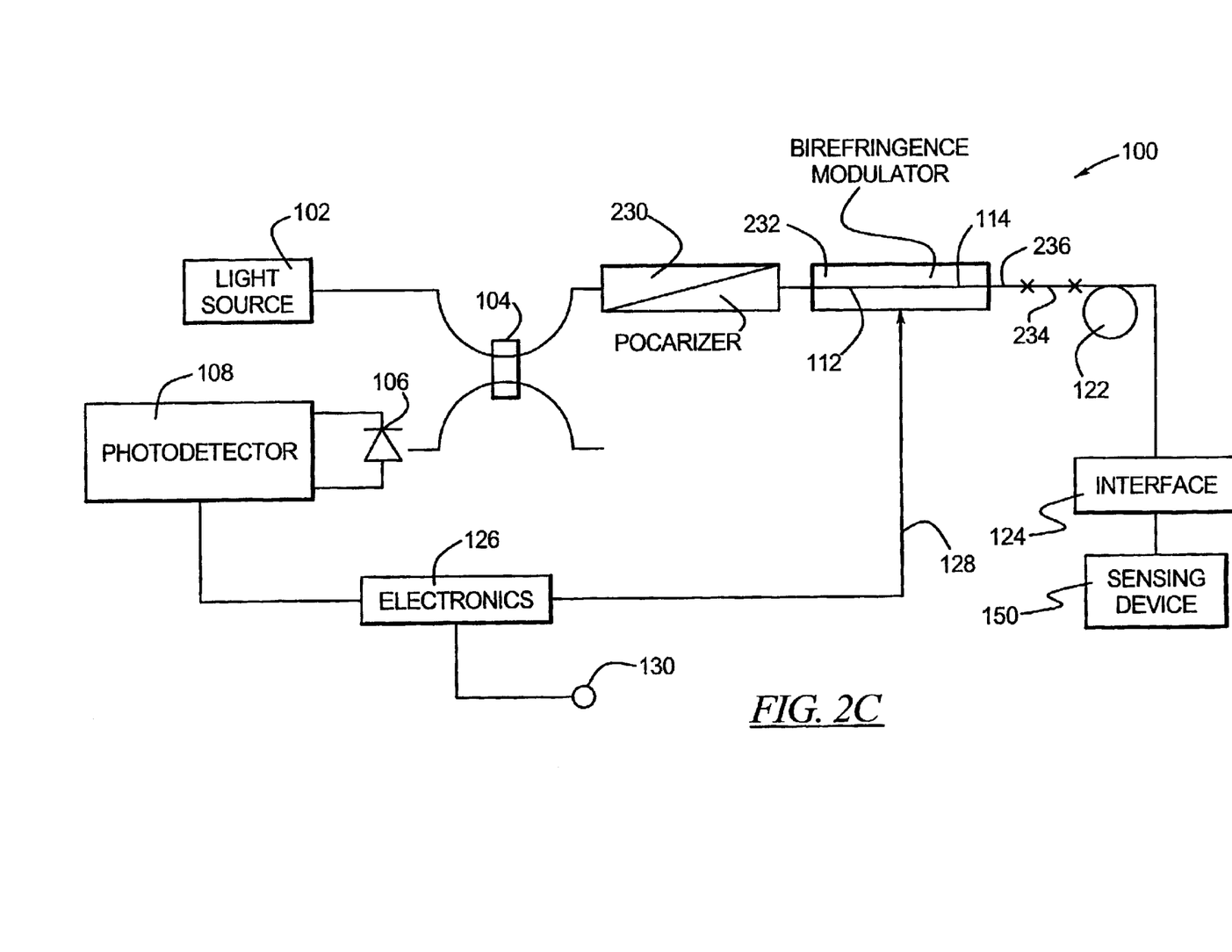
FIG. 2C is a block diagram of a fourth exemplary embodiment of a sensor using birefringence modulation in which the two paths 112 and 114 are the TE and ™ polarization modes.

The basic concepts described above and below could be applied to any number of equivalent devices that produce a sensor output 130 based upon a sensed interference of two light signals. FIGS. 2A, 2B and 2C are schematics of exemplary alternate embodiments of sensors. With reference to FIG. 2A, various embodiments of sensor 100 may eliminate coupler 120 and replace IOC 107 shown in FIG. 1 with a modified IOC 107 as shown in FIG. 2. With reference to FIG. 2B, IOC 107 is eliminated altogether and replaced with a coupler 202 and a phase modulator 204. Phase modulator 204 may be a piezoelectric modulator or any other type of phase-modifying device. Coupler 202 is any conventional coupler such as is described above in conjunction with couplers 104 and 120. Moreover, it is not necessary to modulate the phase of light passing through path 112 to produce an appropriate output signal 130. With reference to FIG. 2C, IOC 107 is replaced with a polarizer 230, a birefringence modulator 232, and a depolarizer 234. In such embodiments, the polarization of light passing through modulator 232 is modulated by signal 128, using the techniques described herein, to produce a transverse magnetic (TM) mode and a transverse electric (TE) mode having different (e.g., orthogonal) polarizations. Interference between the TM and TE signals can then be detected at photodiode 106, as described above. Polarizer 230 is nominally shown in FIG. 2C as a 45-degree polarizer, although any angle of polarization except zero or ninety degrees could be used. Sensor 100 may also include a portion 236 of polarization-maintaining fiber to transmit the two modes from modulator 232 to depolarizer 234. Hence, an interference pattern may be produced at detector 106 even though sensor 100 includes but a single physical path 112/114. The terms "splitter" or "splitting means" as used herein, then, may refer not only to a fiber splitter but also to any structure that creates two or more optical paths. Other embodiments of sensor 100 suitably modulate signal amplitude, frequency or other characteristics of light passing through the sensor to produce distinct but interfering light paths or modes. As noted above, any of the components described as part of sensor 100 may be replaced by equivalent bulk optics components such as modulators, couplers, and the like.

Figure 3:
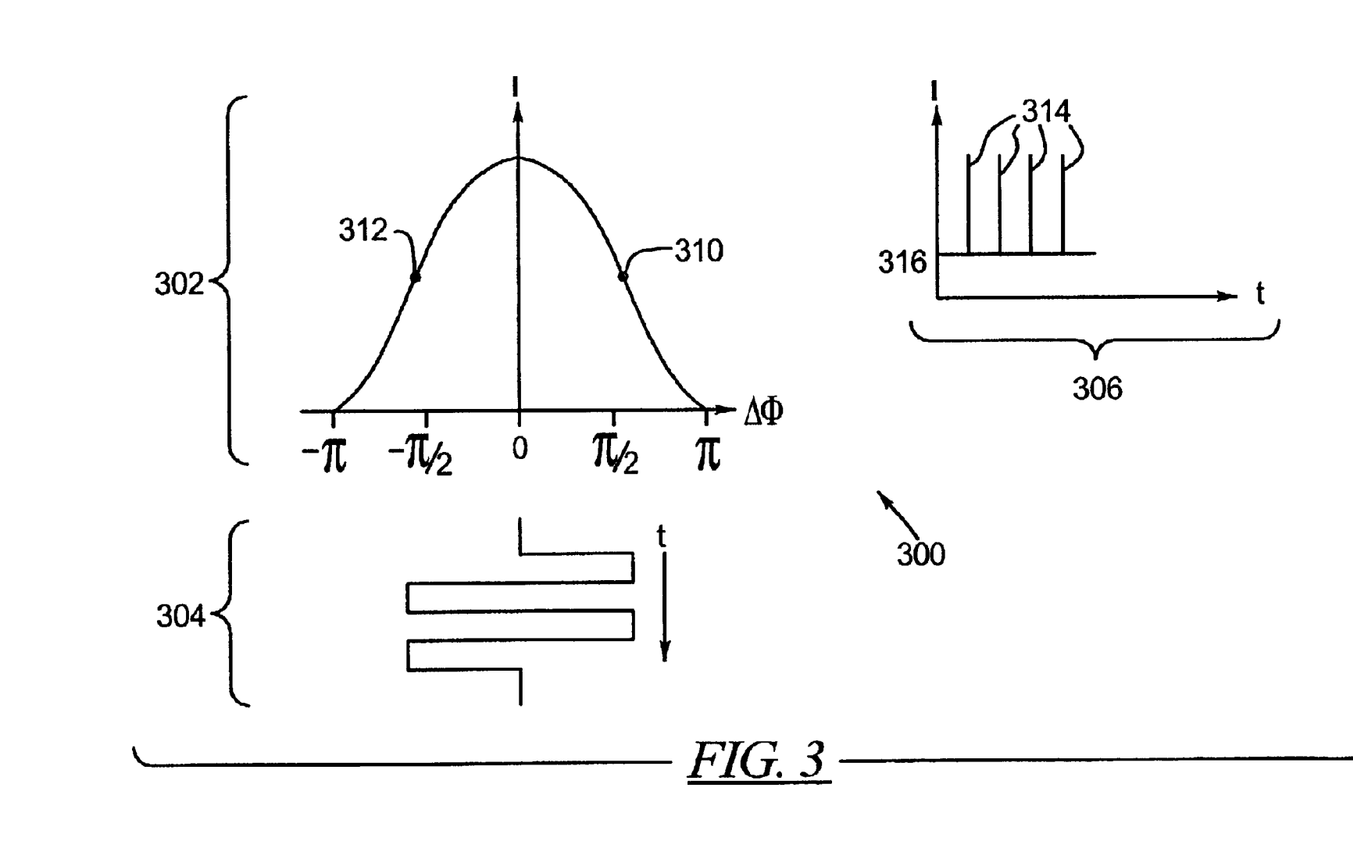
FIG. 3 is a graph of various performance characteristics for an exemplary sensor.

With reference now to FIG. 3, an exemplary output characteristic 300 for a sensor operating at a "proper" frequency is shown. With reference now to FIG. 3, an interferogram 302 suitably plots the intensity of light impinging on photodetector 106 versus the phase shift $\Delta\phi$ observed between the two light beams propagating in sensor 100. As can be appreciated, the intensity of the light is suitably maximized when the light beams are in phase (corresponding to zero phase shift or any integer multiple of $+/-2\pi$ phase shift). Similarly, the intensity of the light is suitably minimized when the light beams are out of phase (corresponding to $\pi$ phase shift, or any odd integer multiple of $+/-\pi$).

When the sensor operates near a maximum or minimum point on interferogram 302, however, changes in phase ($\Delta\phi$) produce only small changes in the intensity of light (I). Moreover, it may be difficult to detect the magnitude of changes in phase from the intensity of light at such operating points, since the curve decreases in both directions departing from the maximum points and increases in both directions departing the minimum points. Various embodiments may therefore bias the gyro to a more sensitive operating point, such as point 310 or point 312 on interferogram 302, which correspond to phase shifts of $\pi/2$ and $\pi/2$, respectively. Of course any odd integer multiple of $+/-\pi/2$ would produce a similar result. This modulation may be produced with "drive" modulation 304, which corresponds to modulation signal 128 in FIGS. 1 and 2 as described more fully below in connection with FIG. 4. As shown in FIG. 3, bias modulation 304 is an alternating bias signal that produces phase biases of $+/-\pi/2$ radians between the two beams propagating in sensor 100. It will be appreciated that any modulation 304 could be provided according to the particular characteristics and needs of the particular embodiment.

As the two beams are biased in accordance with modulation 304, then, the output intensity of light incident upon detector 108 over time ("time waveform") may be as shown in plot 306 in FIG. 3. As can be seen from plot 306, the output intensity of the light (I) is relatively constant at the level 316 corresponding to points 310 and 312 on interferogram 302, with momentary "spikes" 314 resulting from the transition in operating points from point 310 to point 312, and vice versa. Level 316 may also include a component from the two paths, paths 112 and 114, that do not interfere. Spikes 314 may be filtered, ignored, or otherwise processed by electronics 126 (FIG. 1) such that the relatively constant output level 316 may be observed.

Figure 4:
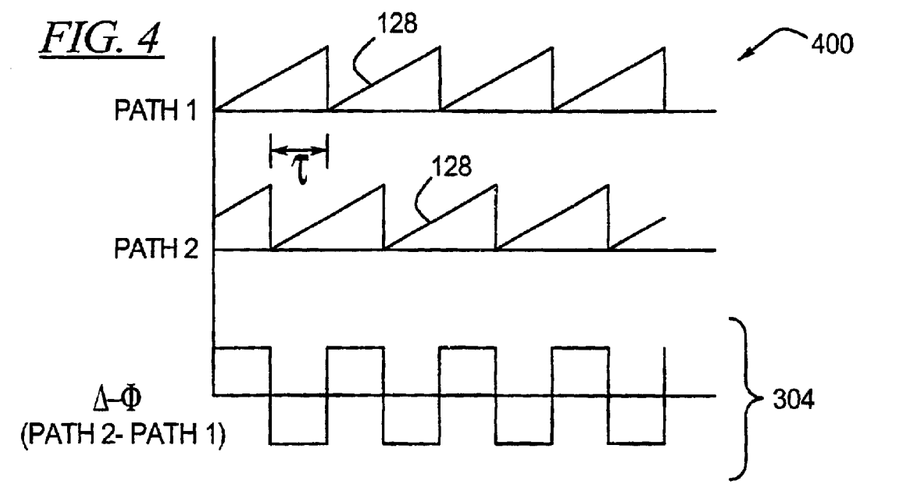
FIG. 4 is a graph of various exemplary modulation signals at a "proper" frequency.

FIG. 4 is a plot of an exemplary modulation technique applied at a proper frequency that may be used to generate modulation 304. With momentary reference to FIGS. 1 and 4, bias modulation signal 128 is generated by electronics processor 126 and provided to modulator 116 to modulate light traveling on waveguide 114. As described above, each beam of light involved in creating interferogram 302 (FIG. 3) passes through waveguide 114, but at a different time (e.g., a first beam passes through waveguide 114 on the way to the sensed device, the second beam passes through waveguide 114 after being reflected by the sensed device). The modulations applied to the two beams, then, are suitably identical but shifted in time according to a delay constant (T) of the sensor, which is related to the path length of the light beam.

With reference now to FIGS. 1 and 4, an exemplary modulation drive signal 128 is suitably a sawtooth waveform having an amplitude tailored to modulator 116 such that the desired phase shift is produced, and having a frequency that is tuned to the "proper" frequency of sensor 100. Numerous techniques for sensing "proper" frequency have been used in conjunction with FOGs and other sensors (see, e.g., U.S. Pat. No. 5,734,469, incorporated herein by reference and a patent application being filed concurrently herewith, whose title is "A Saw Tooth Bias Modulation and Loop Closure for an IFOG and Sagnac Interferometers", by inventor Charles Lange, and identified by Honeywell Docket Number: H17-25172, also incorporated by reference), and any technique for sensing "proper" frequency could be used with the disclosed sensors. Similarly, modulation signal 128 may be any digital or analog serrodyne, triangle, ramp, dual ramp, pulse, step or other waveform, as appropriate, or may incorporate characteristics of multiple waveforms. As can be readily observed from FIG. 4, the modulations applied to the two beams counter-propagating in sensor 100 are identical but shifted in time by delay constant T. The difference between these two signals is shown as signal $\Delta\phi$ 304, which corresponds to signal 304 in FIG. 3. Again, any drive modulation signal 128 that produces a desired phase modulation 304 may be used in various embodiments of sensor 100.

Figure 5:
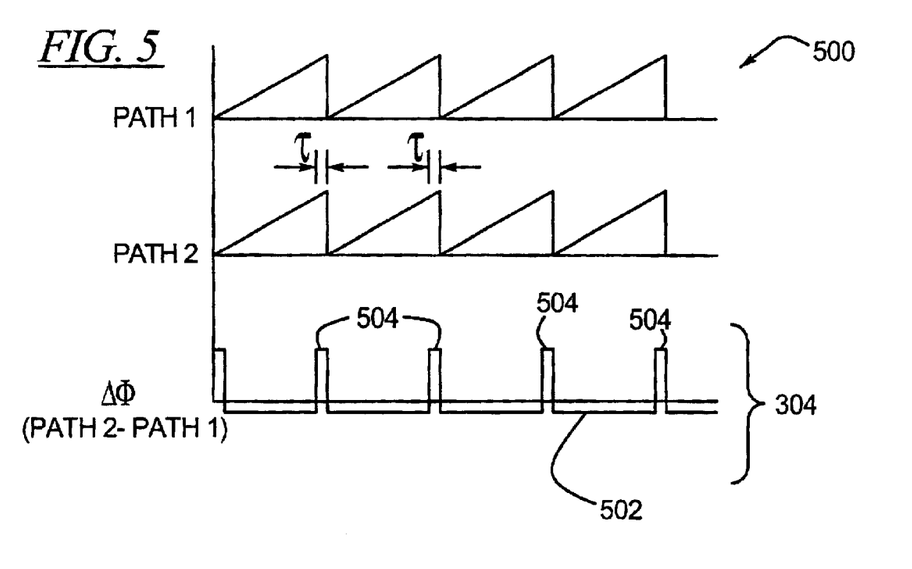
FIG. 5 is a graph of various exemplary modulation signals that are not at a "proper" frequency.

FIG. 5 is a plot of an exemplary modulation technique that is not applied at a proper frequency. With reference now to FIGS. 1 and 5, a drive modulation signal 128 is applied to modulator 116, as described above, but the frequency of signal 128 is not tuned to a proper frequency that is related to the delay constant T. Hence, the difference in phase (Δφ) 304 between beam 1 and beam 2 does not produce a balanced phase modulation signal like that described above. Rather, the difference 304 between the two beams may be characterized by relatively long periods of bias at level 502 interspersed by relatively short periods (corresponding to time T) of bias 504 in an opposite direction and with much larger magnitude than level 502.

Figure 6:
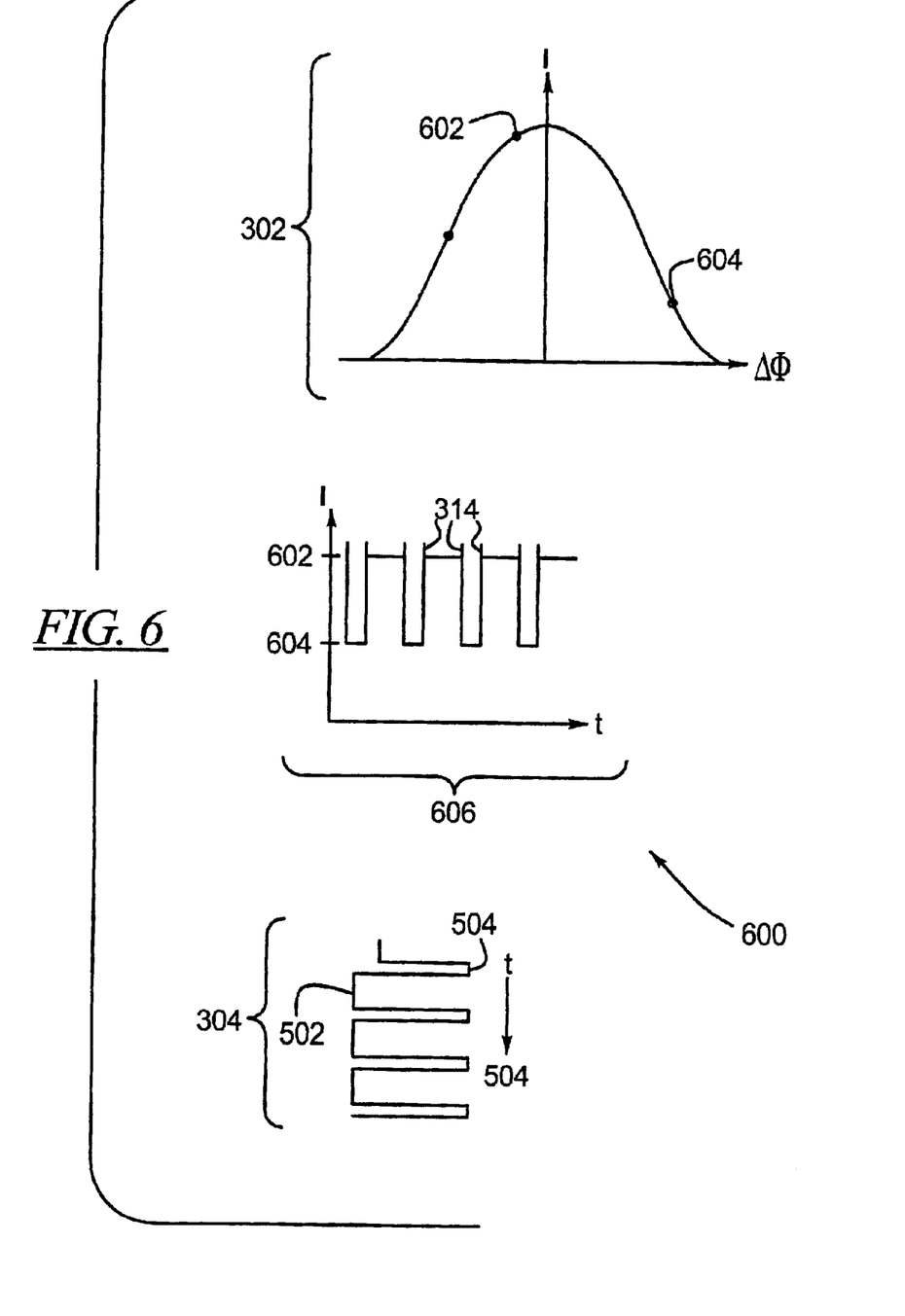
FIG. 6 is a graph of various performance characteristics for an exemplary sensor that is not operating at the "proper" frequency.

An exemplary output characteristic 600 that corresponds to the modulation Δφ 304 shown in FIG. 5 is shown in FIG. 6. With reference to FIG. 6, drive modulation 304 applied to interferogram 302 suitably produces an output characteristic (time waveform) 606 at photodetector 108. As can be seen from the Figure, points 504 on modulation 304 correspond to point 604 on interferogram 302 and output plot 606. Points 502 on modulation 304 correspond to points 602 on interferogram 302 at output plot 606. Hence, the light intensity observed at photodetector 108 suitably alternates between levels 602 and 604.

Comparing and contrasting plot 606 with plot 306 in FIG. 3, the time waveform of the light intensity incident upon photodetector 108 is dependent upon the frequency of the modulation signal, and the "proper" frequency of the modulation signal (i.e., the frequency that produces a relatively constant output at photodetector 108) is dependent upon the time that light takes to pass to, through, and from sensor 100. It therefore follows that the proper modulation frequency is related to the length of the light path. Consequently, the output 130 may be determined from the modulation that results in relatively constant output at detector 108, or in any other suitable desired effect upon the detector output. Stated another way, the length of the optical path can be readily determined as a function of the "proper" modulation frequency that produces a relatively constant output at detector 108.

Adjustments to modulation signal 128 may be performed by a microcontroller, microprocessor, digital signal processor or other controller associated with electronics 130. In an exemplary embodiment, the detector output is sampled at a frequency at least as high as the frequency of modulation signal 128 such that changes in the detector output may be identified. As the frequency of modulation signal 128 approaches the "proper" frequency for the length of the optical path, changes in the detector output are suitably reduced. When an exemplary sensor 100 is modulated at a "proper" frequency, the output characteristic appears as in FIG. 3. When the sensor is modulated at a frequency that is not "proper" for the particular path length, output characteristics observed at detector 108 may be skewed, as shown in FIG. 6, for example. Accordingly, by attempting to maintain the detector output at a desired level, the length of the optical path traveled by the light in sensor 100 may be readily calculated from said proper frequency using a lookup table, mathematical formula, or other technique. This concept may be used to create various sensor devices such as LIDARs, break testers, fiber length testers, range finders, strain sensors, or the like.

Figure 7:
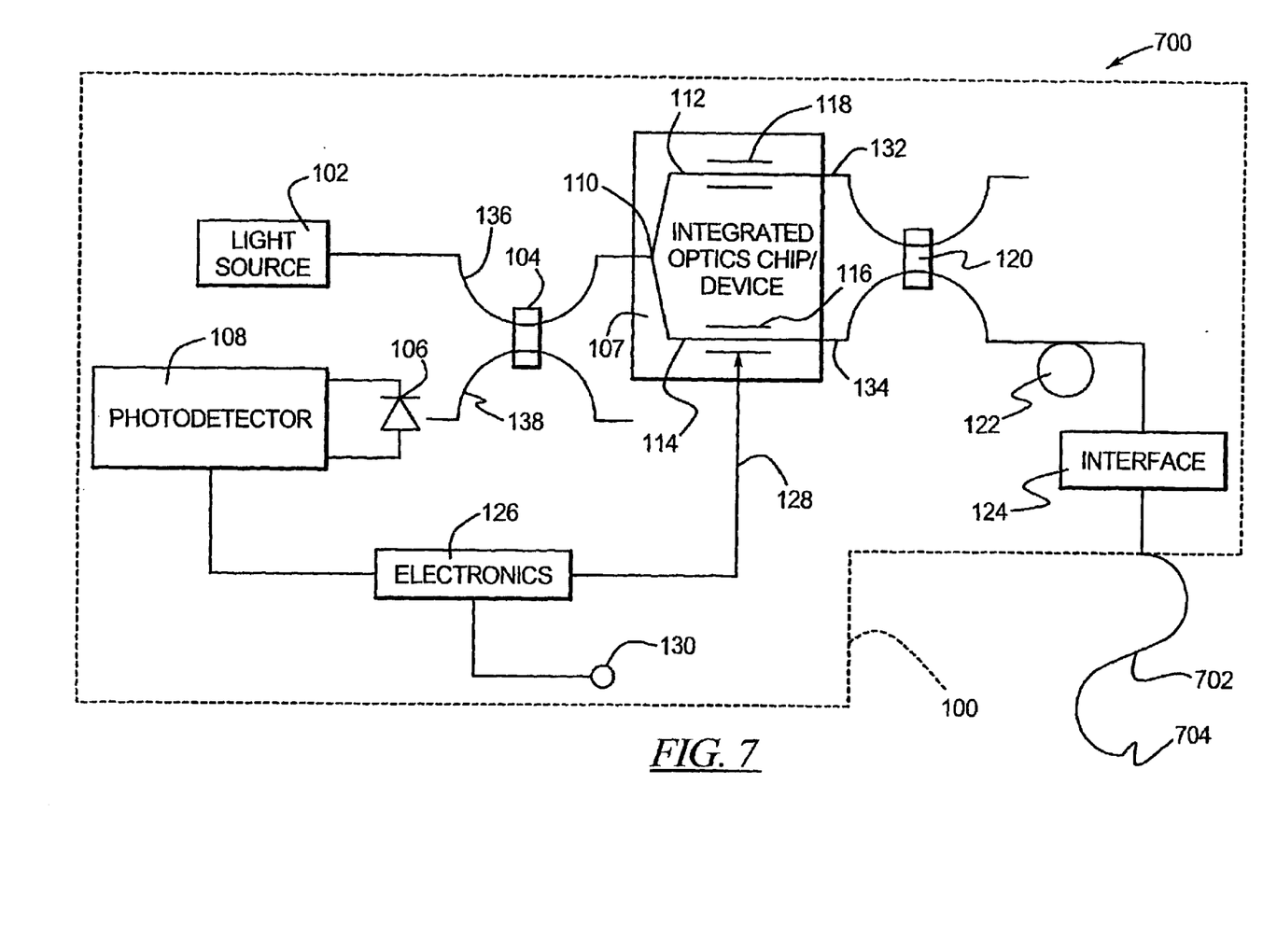
FIG. 7 is a block diagram of an exemplary strain sensor.

FIG. 7 is a block diagram of a strain sensor based upon the concepts described above. With reference to FIG. 7, a strain sensor 700 suitably includes an active sensing element 702 coupled to a sensor 100 as described above. Active sensing element 702 may be made of any material capable of changing the optical path of light passing through it in response to environmental conditions such as temperature, pressure, breaks or stresses, properties of chemical species or the like. In an exemplary embodiment, active sensing element 702 is a single mode optical fiber having a cleaved and polished end 704 suitable for reflecting optical signals. As the fiber expands, contracts or otherwise reacts to environmental changes, the total optical path length of light passing though the fiber suitably changes. These various strains on sensing element 702, however minute, may be sensed using the interferometric modulation techniques described above. The particular type of fiber selected will vary from embodiment to embodiment as certain types of fiber cladding, cores, etc. may be more susceptible than others to changes in temperature, pressure, chemical species or the like.

Although the exemplary embodiment 700 shown in FIG. 7 includes a delay loop 122 and an interface 124, other embodiments may eliminate these elements, and sensing element 702 may be connected to sensor 100 in any manner. Additionally, the length of sensing element 702 may vary widely from embodiment to embodiment depending upon the type of sensor 700 created, and the desired sensitivity. Furthermore, an increased surface area of sensing element 702 exposed to the environment will generally produce heightened sensitivity. Coils of optical fiber (such as relatively inexpensive single mode optical fiber) may be readily produced on the order of 1000 m or more in length, thus enabling a highly sensitive sensor 700. Alternatively, the sensing element may be on the order of a meter or less in length.

Strain sensors 700 may be used in a wide variety of environments. In the various embodiments, environmental conditions such as temperature, pressure, chemical effects and the like suitably produce a strain in sensing element 702 that affects the length of a light path through the element. For example, sensing elements 702 could be placed within wood, metal, concrete or other structures to detect stresses or strain in bridges, dams, roads and the like. Similarly, sensing elements 702 could be embedded or affixed to an aircraft wing to detect stresses, overloading, and the like.

Sensors 700 could additionally be formulated for chemical composition measurements by, for example, removing the cladding on an optical fiber and exposing the optical fiber as a sensing element 702 to a chemical species. Changes in the optical path of sensing element 702 are suitably produced according to the species index of refraction. Further embodiments incorporate a sensing element 702 in thermal contact with a fluid such that fluid temperature fluctuations may be sensed. It will be appreciated that a wide array of applications could be envisioned by exposing sensing element 702 to an environment and measuring effects upon the optical path length of light signals passing through sensing element 702. Effects of these environmental conditions may therefore be correlated to the change in path length, and may be computed through any technique. Correlation between path length and environmental effects may be observed, correlated and/or calculated according to any technique. In an exemplary embodiment, environmental variables are correlated to changes in path length in a lookup table stored in the electronics processor 126, or in an external digital computer in communication with the electronics processor 126.

Figure 8:
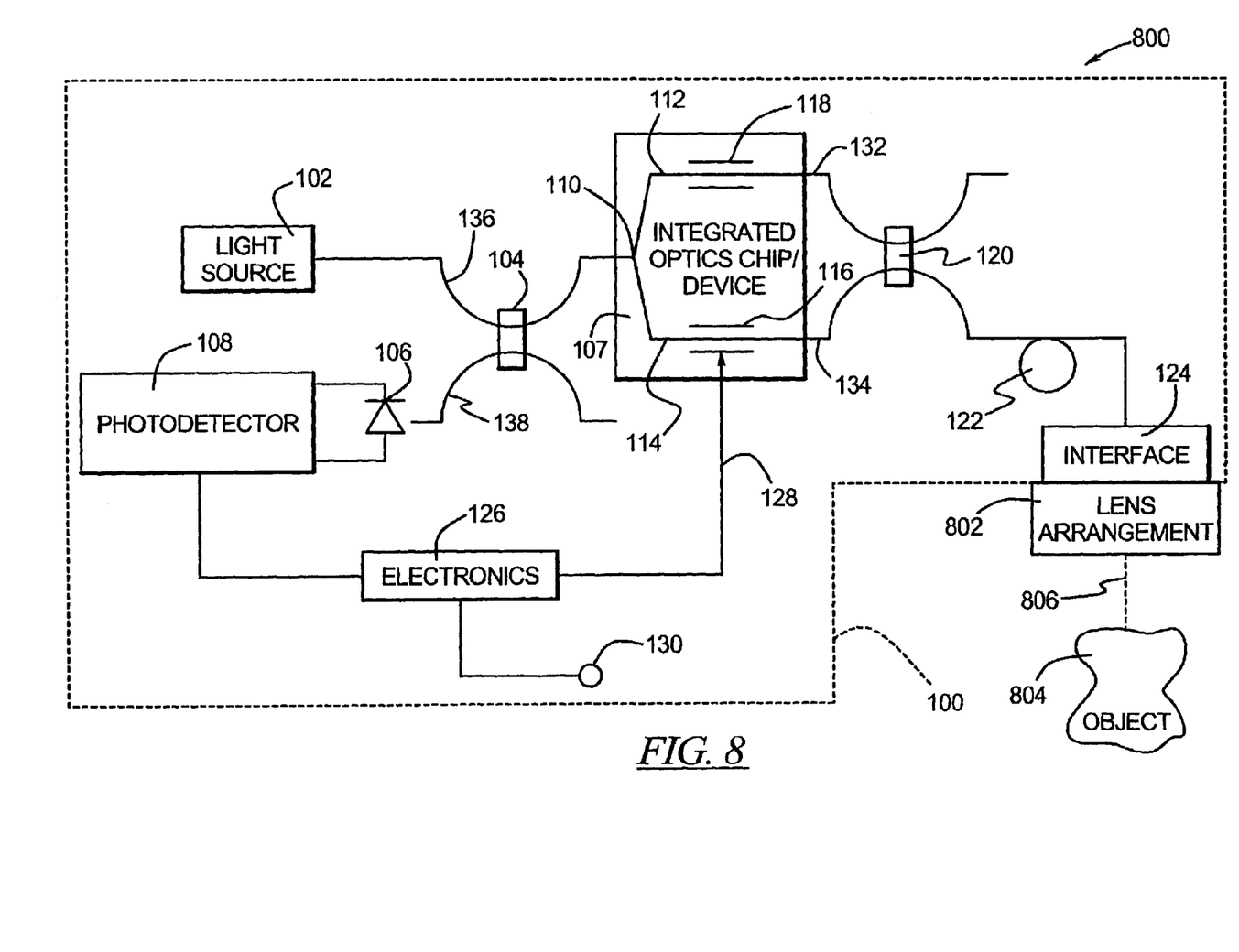
FIG. 8 is a block diagram of an exemplary LIDAR.

FIG. 8 is a block diagram of an exemplary embodiment of a LIDAR 800 based upon interferometric sensing techniques. With reference to FIG. 8, an optical sensor 100 as discussed above may be coupled to a lens arrangement 802 to produce a light beam 806 that is capable of reflecting off of an object 804. Using the interferometric modulation techniques described above, the distance to object 804 may be readily determined. The optical path length detected by sensor 100 is not confined to a waveguide or other path.

Figure 9:
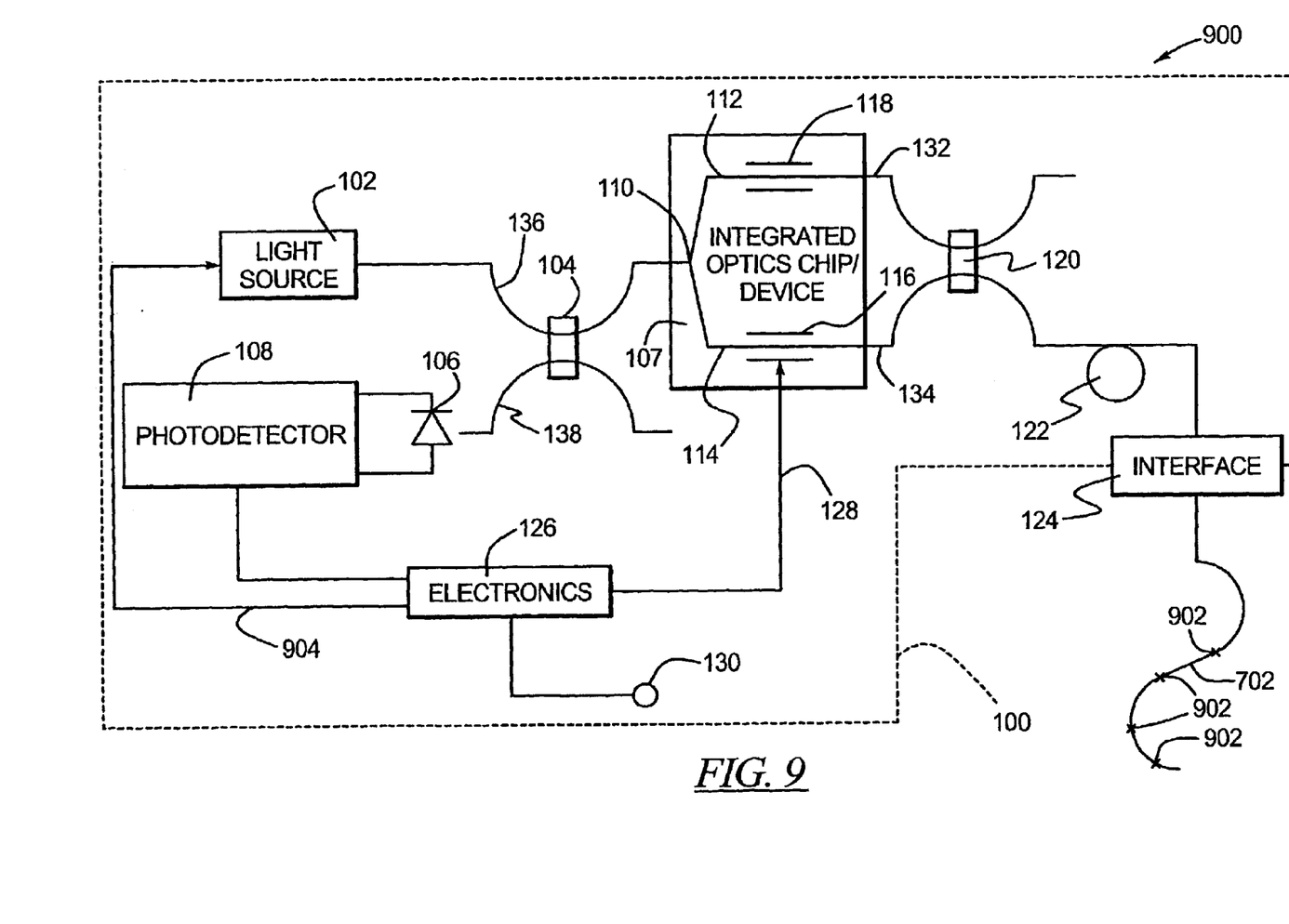
FIG. 9 is a block diagram of an exemplary fiber break detector.

FIG. 9 is a block diagram of an exemplary fiber break detector based upon interferometric sensing techniques. With reference to FIG. 9, a fiber break sensor 900 suitably includes a sensing element 702 including a number of reflective elements 902. In an exemplary embodiment, sensing element is an optical fiber used in communications or other applications. Reflective elements are any joints, gratings, obstructions or other elements present in sensing element 702 capable of reflecting light generated by light source 102. A light source control signal 904 may be provided from electronics 126 to light source 102 to modulate, modify or otherwise adjust the frequency, phase, amplitude or other characteristics of light emanating from light source 102 such that multiple light signals may be reflected off the various reflective elements 902. By verifying continuity between light source 102 and each of the reflective elements 902, breaks in sensing element 702 may be identified and localized.

In an exemplary embodiment, reflective elements 902 are simply fiber splices that have been made such that some light passing through the fiber is reflected by the splice. Such a splice may be made, for example, by intentionally mismatching optical fibers by a very slight distance in a conventional fiber splice, or by splicing fibers of different sizes together. Alternatively, reflective elements 902 may be fiber Bragg gratings tuned to various wavelengths, chirped gratings, or the like as described more fully below.

A number of modulation techniques could be used to monitor light reflecting from the various reflective elements 902 in sensing element 702. Time domain multiplexing (TDM), for example, could be used by simply modulating a proper frequency for a path length corresponding to a first reflective element 902, verifying the presence or absence of a light signal at detector 108, and then moving on to modulate proper frequencies of subsequent reflective elements 902. Alternatively, various light signals could be applied to the sensing element 702 using wavelength division multiplexing (WDM) techniques.

In an example of such embodiments, reflective elements 902 are fiber Bragg gratings that are each tuned to a distinct wavelength of light. Light of varying wavelengths may then be applied to sensing element 702, and reflected signals may be monitored and correlated. Because each grating is sensitive to a light of a particular wavelength, continuity to each grating can then be verified and any breaks in the fiber can be localized. Alternatively, chirped gratings could be used in conjunction with wavelength division multiplexing techniques to increase the optical path length variation within sensing element 702. In yet another embodiment, frequency division multiplexing (FDM) may be used by modulating the frequency of light applied using the known proper frequencies of light returning from the various reflecting elements 902. These multiplexing techniques allow interrogation of multiple sensing elements, thereby detecting and measuring environmental effects at many locations in time and space. Thus the sensor may be used for distributed, rather than single-point sensing, of environmental effects such as temperature, strain, chemical properties, etc.

The proper frequency applied to light signals within sensor 900 is generally inversely proportional to the length of the optical path. Because of this relationship, in various embodiments (particularly those using FDM techniques) it may be generally undesirable to space reflective elements 902 at even multiples of any particular distance (e.g., 1000 m, 2000 m, 4000 m, etc. from the end of the fiber), since the corresponding proper frequencies of such embodiments may produce harmonics that interfere with each other or are difficult to detect. This phenomenon may be reduced or eliminated using delay loop 122 in various embodiments, however. By including even a short delay into the optical path traveled by light in sensor 900, the total light path observed by sensor 100 will be modified such that harmonics are reduced or eliminated. If reflective elements 902 are placed at 1000, 2000 and 4000 meters in sensing element 702, for example, and delay loop 122 is one meter in length, the total optical paths to the various reflective elements will be 1001, 2001 and 4001 meters. Accordingly, harmonics and any associated sources of error are reduced as appropriate. The numbers used herein are for exemplary purposes only, and practical embodiments may use any value for fiber lengths, delay loop lengths, reflector location and the like.

Any number of sensors may be created based upon the various structures and interferometric modulation techniques described above. Strain sensors, break testers, LIDARs and the like may be constructed by sensing the length of an optical path through a sensing element 702. The length of the optical path may be determined with great accuracy by determining the "proper" frequency of a modulation applied to the light that suitably reduces or minimizes the amount of fluctuation observed at a detector 108. Such interferometric techniques are highly accurate, since the factor being controlled and observed is the frequency of an applied modulation.

The corresponding structures, materials, acts and equivalents of all elements in the claims below are intended to include any structure, material or acts for performing the functions in combination with other claimed elements as specifically claimed. Moreover, the steps recited in any method claims may be executed in any order. The scope of the invention should be determined by the appended claims and their legal equivalents, rather than by the examples given above. No element described herein is essential to the practice of the invention unless specifically described as "necessary" or "required".

What is claimed is:

1. A method of sensing an environmental effect upon a sensing element, the method comprising:
    exposing said sensing element to said environmental effect;
    producing a light signal in said sensing element;
    modulating said light signal with a modulation drive signal;
    observing the resulting time-varying output waveform on an optical detector onto which said light signal impinges;
    determining a path length of said light signal from said time-varying output waveform as a function of said modulation signal; and
    providing an output indicative of said environmental effect based on said path length;
    wherein said determining a path length further comprises adjusting said modulation drive signal to determine a proper frequency of said light signal.

2. The method of claim 1, further comprising correlating said path length to said environmental effect.

3. The method of claim 1, further comprising demodulating said time-varying output waveform synchronously with or with reference to the modulation drive signal.

4. The method of claim 1, wherein said sensing element comprises an optical fiber.

5. The method of claim 4, wherein said optical fiber comprises a plurality of reflecting elements and senses a plurality of environmental effects.

6. The method of claim 5, further comprising modulating said light signal to determine path lengths for each of said plurality of reflecting elements.

7. The method of claim 5, further comprising analyzing said time-varying output waveform via Fourier, wavelet, cluster, or other spectral or time-domain techniques to determine proper frequencies of a plurality of said light signals.

8. The method of claim 1, wherein said sensing element comprises a range-finding apparatus.

9. A sensor for determining an environmental effect, the sensor comprising:

a light source producing a light;

a sensing element optically coupled to said light source such that said light propagates through said sensing element;

a detector optically coupled to said sensing element, said detector being configured to detect an intensity of said light propagating in said sensing element and to produce a detector output indicative of said intensity; and, an electronics processor having a receiver to receive said detector output and logic to produce a modulation drive signal for said light based on said detector output, said electronics processor further having an output at which said electronics processor produces an output signal indicative of said environmental effect as a function of said modulation signal and an adjustment mechanism configured to adjust said modulation signal to determine a proper frequency of said output signal.

10. The sensor of claim 9, wherein said modulation signal is provided to said light at a proper frequency that is a function of an optical path length of said light propagating in said sensing element.

11. The sensor of claim 10, wherein said output signal is a function of said proper frequency.

12. The sensor of claim 9, wherein said sensing element is an optical fiber sensitive to said environmental effect.

13. The sensor of claim 12, wherein said optical fiber comprises a plurality of reflective elements configured to reflect said light propagating in said optical fiber.

14. The sensor of claim 13, wherein said electronics processor has a further output to provide a modulation signal to said light, and wherein said light is modulated by said modulation signal such that a portion of said light is reflected by each of said reflective elements.

15. The sensor of claim 14, wherein said electronics processor is further configured to sense said portion of said light reflected by each of said reflective elements.

16. The sensor of claim 9, wherein said environmental effect comprises a strain on said sensing element.

17. The sensor of claim 16, wherein said strain is caused by or correlated with pressure.

18. The sensor of claim 16, wherein said strain is caused by or correlated with temperature.

19. The sensor of claim 16, wherein said strain is caused by or correlated with a chemical.

20. A sensor for determining an environmental effect, the sensor comprising:

a light source producing a light;

a sensing element optically coupled to said light source such that said light propagates through said sensing element;

a detector optically coupled to said sensing element, said detector being configured to detect an intensity of said light propagating in said sensing element and to produce a detector output indicative of said intensity;

an electronics processor having a receiver to receive said detector output and to produce a modulation signal for said light based on said detector output, said electronics processor further having an output at which said electronics processor produces an output signal indicative of said environmental effect as a function of said modulation signal;

an integrated optics device connected to said electronics processor and further connected to a first optical coupler, said first optical coupler being connected to said light source and said detector, said integrated optics device being further connected to a second optical coupler, said second optical coupler being connected to said sensing element; and an adjustment mechanism configured to adjust said modulation signal to determine a proper frequency of said output signal.

21. The sensor of claim 20, further comprising:

a delay loop that adds additional optical path length and is positioned between said integrated optics device and said sensing element; and an interface positioned between said delay loop and said sensing element.

22. The sensor of claim 20, wherein said integrated optics device comprises:

a Y-junction that separates light into two components on a first light path and a second light path; and, at least one phase modulator that modulates light on at least one light path, said at least one phase modulator being connected to said modulation signal of said electronics processor.

23. A method of sensing an environmental effect upon a sensing element, the method comprising:

exposing said sensing element to said environmental effect;

producing a light signal in said sensing element;

modulating said light signal with a modulation signal;

determining a path length of said light signal as a function of a time delay in said modulated light signal;

providing an output indicative of said environmental effect based on said path length; and wherein said determining a path length further comprises adjusting said modulation signal to determine a proper frequency of said light signal.

* * * * *

UNITED STATES PATENT AND TRADEMARK OFFICE
CERTIFICATE OF CORRECTION

PATENT NO. : 6,778,279 B2
DATED : August 17, 2004
INVENTOR(S) : Charles Lange et al.

It is certified that error appears in the above-identified patent and that said Letters Patent is hereby corrected as shown below:

<u>Column 2,</u>
Line 44, change "TE and $^{TM}$" to -- TE and TM --.

Signed and Sealed this

Twenty-fourth Day of May, 2005

JON W. DUDAS
*Director of the United States Patent and Trademark Office*